United States Patent [19]

Hochmair et al.

[11] Patent Number: 4,593,696
[45] Date of Patent: Jun. 10, 1986

[54] AUDITORY STIMULATION USING CW AND PULSED SIGNALS

[76] Inventors: Ingeborg J. Hochmair; Erwin S. Hochmair, both of A-1130 Wien Jaunerstrafse 27, Vienna, Austria

[21] Appl. No.: 692,246

[22] Filed: Jan. 17, 1985

[51] Int. Cl.[4] .............................................. A61N 1/18
[52] U.S. Cl. ................................ 128/419 R; 128/784; 179/107 E; 381/68
[58] Field of Search ........... 128/746, 1 R, 784, 419 R, 128/789; 381/68, 46, 50; 179/107 E, 107 BC

[56] References Cited

U.S. PATENT DOCUMENTS

| | | | |
|---|---|---|---|
| 4,357,497 | 11/1982 | Hochmair et al. | 179/107 E |
| 4,419,995 | 12/1983 | Hochmair et al. | 128/784 |
| 4,428,377 | 1/1984 | Zollner et al. | 128/419 R |
| 4,441,202 | 4/1984 | Tong et al. | 381/68 |

Primary Examiner—Kyle L. Howell
Assistant Examiner—Daniel Haneiwich
Attorney, Agent, or Firm—Flehr, Hohbach, Test, Albritton & Herbert

[57] ABSTRACT

An improvement in noise susceptibility is realized in auditory stimulation of the deaf by electrical signals. At least one analog electrical signal is applied to implanted electrodes in a patient, and at least one pulsatile signal is applied to implanted electrodes. The analog signal represents a speech signal, and the pulsatile signal provides specific speech features such as formant frequency and pitch frequency.

18 Claims, 4 Drawing Figures

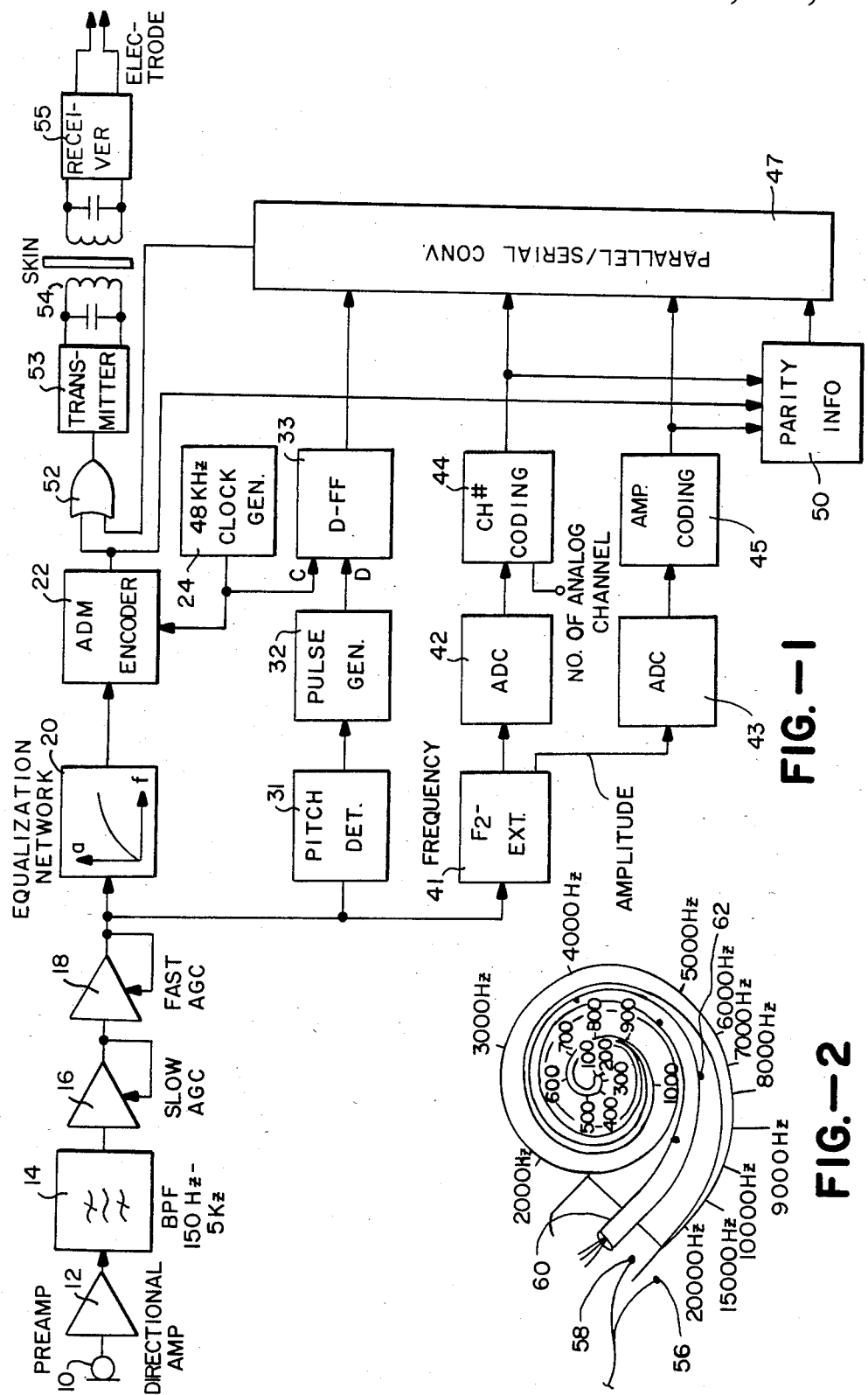

AUDITORY STIMULATION USING CW AND PULSED SIGNALS

This invention relates generally to auditory stimulation systems, and more particularly the invention relates to a method and means for electrical auditory stimulation of the deaf.

Disclosed in our U.S. Pat. Nos. 4,284,856 and 4,357,497 for "Multiple Frequency System and Method for Enhancing Auditory Stimulation and the Like" are transcutaneous auditory stimulation systems in which electrical signals corresponding to different audio frequency bands are transmitted by multi-channel RF transmission means to a coupled transcutaneous receiver. The receiver demodulates the signals, and the signals are then applied as analog signals to a multi-electrode prosthesis implanted in the cochlea.

U.S. Pat. No. 4,419,995 for "Single Channel Auditory Stimulation System" discloses the use of electrodes placed at or near the base of the cochlea for imparting full speech patterns without the need of penetrating the cochlea.

More recently, the use of a pulsatile signal for transmitting auido signals has been proposed. See U.S. Pat. No. 4,441,202 for "Speech Processor". According to this patent an input speech signal is passed through a filter circuit, zero crossing counter, and RMS measuring circuit for producing signals representing amplitude and frequency of the fundamental voicing component and the first three formants of the speech signal. Computer means is then utilized to determine the manner of stimulation of implanted electrodes by ranking the sharpness of the electrodes in assigning sub-bands of the second formant frequency range to particular electrodes. The formant and prosodic information is applied to the electrodes in pulse form.

Users of transcutaneous audio stimulation systems have noted that their understanding rapidly decreases in the presence of background noise. Accordingly, an object of the present invention is an improvement in speech understanding of deaf persons using transcutaneous auditory stimulation systems.

In accordance with the invention at least one analog signal representing the speech signal and at least one pulsatile signal providing specific speech features are concurrently applied for auditory stimulation. Experiments have demonstrated that an unexpected improvement in noise susceptibility can be realized by using a multi-channel transmission system with at least one analog signal transmitted in one channel being combined with at least one pulsatile signal transmitted in another channel.

The analog signal is generated by compressing the audio signal in amplitude, adjusting the compressed signal to match the frequency response of the patient, and then transmitting the analog signal in a channel to the stimulation electrode which gives the best speech understanding. The analog signal preferably has the bandwidth of approximately 100–5,000 Hertz. The at least one pulsatile signal provides certain selected speech features such as first and second formant frequency and speech frequency. These extracted features can be presented to the patient using the first or second formant frequency as the pulse rate with a specific frequency band always presented to a particular electrode channel. Alternatively, the formant frequency can be presented to one particular electrode channel with the stimulating pulse rate being directly derived from the pitch frequency. The pulse amplitude can be proportional to the formant amplitude or to the RMS value of the entire speech signal.

Accordingly, features of the invention include a multi-channel system for auditory stimulation including a multi-electrode prosthesis for cochlea stimulation with transmission and receiver means for providing at least one analog signal and at least one pulsatile signal concurrently to the multi-electrode prosthesis for concurrently stimulating the auditory nerve.

The invention and objects and features thereof will be more readily apparent from the following detailed description and appended claims when taken with the drawing, in which:

FIG. 1 is a functional block diagram of a multi-channel auditory stimulation system in accordance with the invention.

FIG. 2 is a schematic illustrating the placement of electrodes for stimulating the cochlea.

Figure 3:
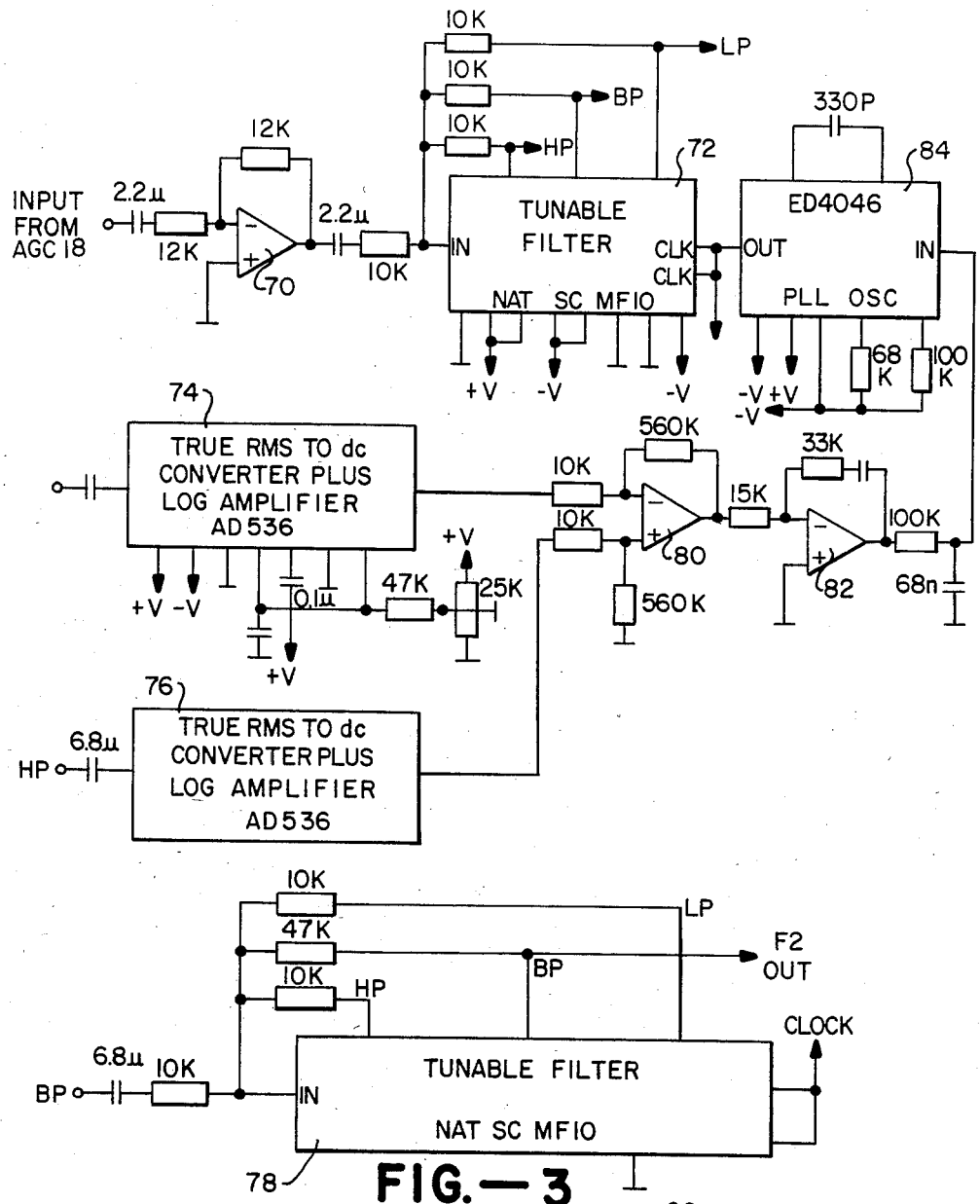
FIG. 3 is a schematic of second formant frequency extraction circuitry.

Referring now to the drawings, FIG. 1 is a functional block diagram of a multichannel speech coding system in accordance with one embodiment of the invention. In this embodiment several transmission and electrode channels are provided. The speech processor contains a microphone 10, a preamplifier 12, and a bandpass filter 14 to limit the frequency range of the audio signal to be processed to the bandwidth necessary for speech transmission (150 Hz to 5 kHz), a slow automatic gain control (AGC) 16 to adjust the audio-amplification to the actual speech level, and a fast AGC (syllabic compression) 18 to enhance the consonant-to-vowel ratio.

Speech is received by microphone 10 and amplified by preamplifier 12. The amplfied speech signals are passed through the bandpass filter 14, the slow gain controlled amplifier 16 and the fast gain controlled amplifier 18 functioning as a syllabic compressor to increase the consonant-to-vowel amplitude ratio in order to fit the speech signals within the narrow dynamic range of the electrically stimulated auditory system.

Thereafter, the signal is processed by several paths in parallel. In the analog path the signal is equalized by the individually adjusted frequency response of a filter network 20 in such a way that all frequencies within the audio band used sound equally loud. This analog signal is then encoded by an adaptive delta modulator (ADM) 22 into a 48 kHz bit stream and applied to OR gate 52.

This channel provides the broad-band analog signal as described in U.S. Pat. No. 4,357,497.

The signals for the pulsatile stimulation channels are interleaved in between the 48 kHz analog channel information as provided by the ADM encoder 22. The pulsatile stimulation channels represent selected features of speech.

The features extracted in this example are pitch ($F_0$), the 2 second formant frequency ($F_2$), and the amplitude $A_2$. Other features which could be selected are, for example, the first formant features $F_1$, $A_1$ and the third formant features, $F_3$ and $A_3$.

In order to provide the patient with reliable pitch and formant estimates in noisy environments where the speech to noise ratio is low, the strategies used are selected from a variety of known possibilities for their robustness, i.e. noise suppression characteristics.

The pitch information is used to generate pulsatile stimulation signals (pulse rate approximately from 100 to 300 pulses/sec) in a 20.8 μs sampling interval detector 31, a pulse generator 32 and D-flip-flop 33 which is driven by the same clock 24 (48 kHz) used for the ADM encoder. Appended to these stimulation pulses, which determine the rate of stimulation, is a coded channel number and the amplitude information. Circuitry 41, described in more detail in FIGS. 3 and 4, extracts the second formant, and the frequency thereof is applied through A-D converter 42 to the channel coder 44. The amplitude is applied through A-D converter 43 to the coding circuit 45. The channel number determines the location within the scala tympani of the electrode contact to be used for stimulation. This provides some tonotopic information in addition to the temporal information provided by the analog channel. The redundancy thus obtained is intended to help the patient to recognize speech sounds also in noise environments. The channel number, as well as the amplitude information is obtained from the $F_2$-extraction circuit 41. The number of the channel which is to be reserved for the analog signal is set by a number of switches. The data from flip-flop 33, coder 44, and coder 45 are multiplexed in parallel to serial converter 47 and then applied to OR gate 52. The signals for all the different stimulation channels are transmitted by one rf-carrier in transmitter 53.

The digitally encoded information for the pulsatile stimulation is combined with the digitally encoded information (ADM) for the analog stimulation signal which may be in the same channel or in different transmission channels. A parity check information 50 is appended to this combined signal, which is used to modulate an rf-transmitter providing the transcutaneous link to the implanted receiver as disclosed in our U.S. Pat. No. 4,357,497, supra.

The implanted receiver 55, which is coupled to transmitter 53 by coils 54, comprises a tuned receiver coil, a signal demodulator, a power supply circuit which provides the dc-power necessary to run the implanted circuitry by rectifying the rf-carrier, circuitry for decoding and error detection, and the electrode drivers. All electronic circuitry is encapsulated in a hermetic package.

After converting the serial bit stream provided by the demodulator into parallel form by the serial-parallel converter and after error checking, decoding provides
 (a) the analog stimulation signal (ADM decoder)
 (b) the stimulation pulses of correct amplitude and duration (pulse width and pulse amplitude decoder)
 (c) the channel number, i.e. the stimulation site.

The particular electrode driver which will provide the stimulation current is selected by adequately addressing the multiplexer.

It is possible to simultaneously stimulate the channel selected to receive the analog signal and up to two channels for pulsatile stimulation.

For each patient it is individually decided which electrode channel carries which signal. The broad band analog signal is directed to that channel which gives optimum performance with this signal for best speech understanding by the patient. The remaining channels are ranked according to the timbre they provide and they thus correspond to eight individual formant frequency ranges.

The channel number information necessary to direct the analog stimulation signal and the pulsatile stimulation signals to the electrodes intended, is transmitted together with the amplitude and pulsewidth information.

Choosing a particular electrode channel requires that the corresponding sound-processing channel be adapted to the characteristics of this particular electrode channel (frequency response, discomfort threshold, dynamic range). This is also true for the pulsatile stimulation signals. The specificity of the responses which can be elected via different electrode channels (e.g. dynamic range, discomfort threshold, frequency response) has to be accounted for in the corresponding channels of the sound processor.

Referring now to FIG. 2, electrode structures are illustrated which can be used for stimulating the cochlea. In one embodiment an elongated prosthesis 60 including a plurality of electrodes 62 is inserted within the cochlea to selectively stimulate the cochlea in accordance with the frequency response thereof, in accordance with U.S. Pat. No. 4,357,497, supra. Selected electrodes are connected to the several channels in the transmitter and receiver. Alternatively, electrodes can be provided at the base of the cochlea such as electrodes 56 and 58. As disclosed in U.S. Pat. No. 4,419,995, the active electrode 58 is preferably placed in the round window at the base of the cochlea or on the promontary. The ground electrode 56 is placed 2–10 millimeters from the active electrode to thereby confine the electric field. The two electrodes can be stimulated from the multiple channels, or alternatively a pair of electrodes can be provided for each channel.

Figure 4:
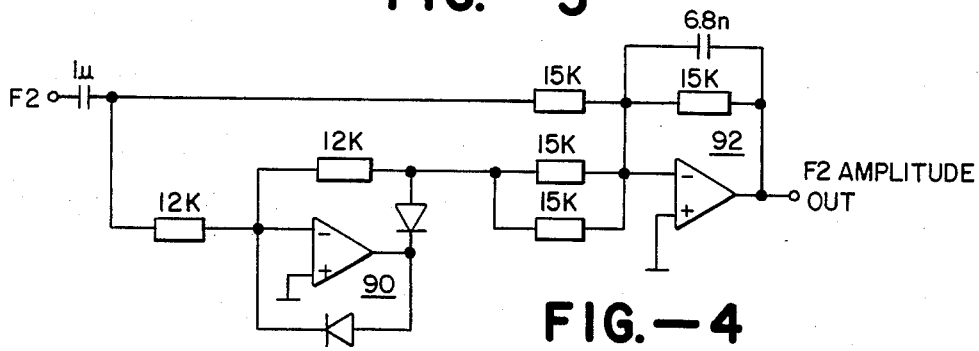
FIG. 4 is a schematic of the second formant amplitude extraction circuitry.

Consider now the circuitry of FIGS. 3 and 4 for extracting second formant frequency and amplitudes. In vowel identification tasks, confusions occur most frequently between vowels with similar first and different second formant. To improve vowel identification with cochlear prostheses, it therefore seems reasonable to present F2-information via one or more channels in addition to the broadband analog speech signal transmitted in the first channel. If the second formant in vowel identification tasks is extracted via speech analysis programs by a computer and presented to patients through a second channel, the scores of the patients in this kind of task seem to be higher than those obtained with the single channel only. But formant tracking using a computer and sophisticated software is not usable with a wearable speech processor. Therefore, a hardware realization for the formant extraction with a minimum number of components and minimized power consumption is necessary.

Tradeoffs between tracking accuracy and circuit complexity are necessary. For example, the second formant is not the only cue in discrimination of vowels, another cue is the center of gravity of the spectrum, which usually, but not always, more or less closely follows second formant location. For very limited systems it is easier to estimate the part of the spectrum where most of the signal energy is concentrated where the second formant is expected. Experiments have been conducted of methods to extract the second formant or to locate the maximum of the spectral density. FIGS. 3 and 4 show the circuit diagrams of one of these methods, the "tunable band pass filter method".

In FIG. 3, the input from AGC 18 is amplified at 70 and applied to tunable filter 72 (National SC MF 10). Lowpass (LP), bandpass (BP), and highpass (HP) outputs from filter 72 are applied to ac converter and log amplifiers 74 and 76 and tunable filter 78, respectively. The outputs of converter-log amplifiers 74 and 76 are subtracted by differential amplifier 80, and the output of amplifier 80 is applied through filter 82 to a phase locked loop 84 (PLL 4045). The output of PLL 82 is applied as the clock signal to filter 72. The output of tunable filter 78 is the F2 frequency output.

A simple bandpass filter being swept over the frequency range of an input signal consecutively outputs the amplitude of the spectral components (integrated over the bandwidth of the filter) of the input signal. If its tuning is controlled in such a way that the output voltage is maximized, the center frequency of the filter indicates the frequency of the maximum of the spectrum. In order to obtain a sufficiently accurate output signal, the filter bandwidth must be compatible with the expected rate of amplitude density change of the spectrum of the (speech) input signal and with the expected sweep rate of the filter as well. The sweep rate again depends on the rate of change of the formant frequencies (approximate second formant) of the input signal. The center frequency can always be tuned in such a way, that the maximum of the amplitude is at the center frequency. Thus the center frequency traces the second formant or the spectral center of gravity. The output of the bandpass filter cannot drive the control circuit directly, because there is no phase information available and so the direction of tuning necessary is unknown. The information for the direction of tuning is gained as follows.

There are a highpass and a lowpass filter tracking the bandpass filter, their cutoff frequencies are the same as the center frequency of the bandpass filter. The control circuit adjusts its output voltage in such a way, that the output voltages of the highpass and the lowpass filter are equal. Such a filter which can produce various second order functions is called a universal filter. The center frequency of the lowpass, highpass and bandpass functions are directly dependent on the external resistor and capacitory values. The center frequency can be changed without changing the quality factor of the filters. The quality factor of the bandpass filter is fixed at 4.7. The center frequency of the tunable filter 72 is directly dependent on the clock frequency from PLL 84. The signal to noise ratio is somewhat low, but this is of no consequence since the dynamic ranges of our patients are small as well. The comparison of the outputs of the lowpass and the highpass is done by a differential amplifier 80. The filter output is applied to voltage controlled oscillator 84 driving the clock input of the universal filter. The clock frequency is proportional to the center frequency of the bandpass filter and thus to the extracted formant as well. FIG. 4 produces the amplitude signal for the second formant. The $F_2$ frequency output from FIG. 3 is applied to the operational amplifier rectification circuit 90, and the rectified output from circuit 90 is applied to lowpass filter 92.

By applying to the implanted electrodes both a continuous wave analog signal representing the speech pattern along with a pulsatile signal representing selected features of the speech pattern, improved speech understanding has been realized by deaf patients by reducing noise susceptibility.

While the invention has been described with reference to a specific embodiment the description is illustrative of the invention and is not to be construed as limiting the invention. For example, the speech processor disclosed in U.S. Pat. No. 4,441,202 can be combined with the processor disclosed in our U.S. Pat. No. 4,357,497 in practicing the invention. Thus, various modifications and applications may occur to those skilled in the art without departing from the true spirit and scope of the invention as defined by the appended claims.

What is claimed is:

1. An auditory stimulating system comprising
 sound processing means for generating analog and pulsatile signals in response to audio signals,
 transmission means for transmitting at least one analog signal indicative of audio sounds and at least one pulsatile signal indicative of features of audio sounds,
 receiver means for receiving said at least one analog signal and at least one pulsatile signal,
 a multi-electrode prosthesis for stimulating the cochlea of a patient, and
 means interconnecting said receiver means and said multi-electrode prosthesis whereby said analog signal and said pulsatile signal concurrently stimulate the auditory nerve.

2. An auditory stimulation system as defined by claim 1 wherein said analog signal is transmitted to at least one prosthesis electrode selected to provide best speech understanding to the patient.

3. The auditory stimulation system as defined by claim 2 wherein said multi-electrode prosthesis is adapted to be inserted into the cochlea, said electrodes corresponding to different audio frequency ranges.

4. The auditory stimulation system as defined by claim 1 wherein said multi-electrode prosthesis comprises electrodes adapted for placement outside of the cochlea for stimulating the auditory nerve.

5. The auditory stimulation system as defined by claim 1 wherein said at least one analog signal and said at least one pulsatile signal are transmitted via separate transmission channels.

6. The auditory stimulation system as defined by claim 1 wherein said sound processing means generates a digitized analog signal, the digitized signal and said pulsatile signal being transmitted as a multiplexed composite signal.

7. The auditory stimulation system as defined by claim 1 wherein said sound processing means generates a pulsatile signal that has a pulse rate corresponding to a formant frequency of a speech input.

8. The auditory stimulation system as defined by claim 1 wherein said sound processing means generates a pulsatile signal that has a pulse rate derived from pitch frequency of a speech input.

9. The auditory stimulation system as defined by claim 1 wherein said sound processing means generates at least two pulsatile signals that are generated and transmitted to said prosthesis electrodes, said two pulsatile signals representing different speech features.

10. The auditory stimulation system as defined by claim 9 wherein said different speech features are pitch frequency and formant frequency.

11. The auditory stimulation system as defined by claim 1 wherein said means interconnecting said at least one analog signal and said at least one pulsatile signal applies said signals to the same electrodes of said prosthesis.

12. An auditory stimulation system as defined by claim 11 wherein said analog signal is transmitted to at least one prosthesis electrode selected to provide best speech understanding by the patient.

13. The auditory stimulation system as defined by claim 12 wherein said multi-electrode prosthesis is adopted to be inserted into the cochlea, said electrodes corresponding to different audio frequency ranges.

14. A method of auditory stimulation of a deaf person comprising the steps of
implanting a multielectrode prosthesis in said person for electrical stimulation of the auditory nerve,
transmitting a broad band analog signal to said multi-electrode prosthesis, and
transmitting a pulsatile signal to said multielectrode prosthesis, said pulsatile signal providing extracted speech features.

15. The method as defined by claim 14 wherein said multielectrode prosthesis is implanted in the cochlea, said analog signal being transmitted to electrodes which provide optimum performance.

16. The method as defined by claim 14 wherein said multielectrode prosthesis includes electrodes placed outside of the cochlea.

17. The method as defined by claim 16 wherein said analog signal and said pulsatile signal are both applied to a pair of electrodes.

18. The method as defined by claim 14 wherein said analog signal and said pulsatile signal are applied to a pair of electrodes.

* * * * *